United States Patent [19]

Huhn et al.

[11] Patent Number: 4,508,658
[45] Date of Patent: Apr. 2, 1985

[54] PENTAHALOPHENYL ESTER OF CYANOACETIC ACID DERIVATIVES

[75] Inventors: Magda Huhn; Gabor Szabo; Peter Dvortsak, all of Budapest; Marianna Karpati, Szeged; Eva Somfai, Budapest, all of Hungary

[73] Assignee: Chinoin Gyogyszer es Vegyeszeti Termekek Gyara Rt., Budapest, Hungary

[21] Appl. No.: 113,380

[22] Filed: Jan. 18, 1980

Related U.S. Application Data

[63] Continuation-in-part of Ser. No. 923,698, Jul. 11, 1978, abandoned.

[30] Foreign Application Priority Data

Jul. 13, 1977 [HU] Hungary ............ CI 1755

[51] Int. Cl.³ .......................... C07C 121/46
[52] U.S. Cl. .................. 260/465 D; 549/496; 549/77; 546/330; 544/22; 544/28
[58] Field of Search ............ 260/465 D, 239.1, 347.4; 542/427; 546/330; 549/77, 496

[56] References Cited

U.S. PATENT DOCUMENTS 2,749,232 6/1956 Ligett et al. .................. 260/465 D
4,171,303 10/1979 Huhn et al. .................. 260/239.1

FOREIGN PATENT DOCUMENTS 843106 10/1976 Belgium .
7807540 7/1978 Netherlands .
2001068 1/1979 United Kingdom .

OTHER PUBLICATIONS

Ziegler et al., Chemical Abstracts, vol. 84, 135413, (1976).

Primary Examiner—Nicky Chan
Attorney, Agent, or Firm—Karl F. Ross; Herbert Dubno

[57] ABSTRACT

Compounds of the formula

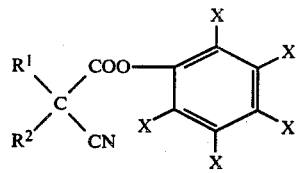

wherein
$R^1$ is hydrogen or $C_1$ to $C_6$ alkyl;
$R^2$ is hydrogen, phenyl, thienyl, furyl, pyridyl, $C_1$ to $C_6$ alkyl, furylalkyl where the alkyl is $C_1$ to $C_6$, or phenylalkyl where the alkyl is $C_1$ to $C_6$; or
$R^1$ and $R^2$ together form $C_1$ to $C_4$ alkylene, furyl-$C_1$ to $C_4$ alkylene or phenyl-$C_1$ to $C_4$ alkylene; and X is halo; or a pharmaceutically acceptable salt thereof, are disclosed as well as a process for the preparation thereof. The new compounds are intermediates useful in the production of penicillins and cephalosporins with antibiotic activity.

9 Claims, No Drawings

PENTAHALOPHENYL ESTER OF CYANOACETIC ACID DERIVATIVES

CROSS REFERENCE TO RELATED APPLICATIONS

This application is a continuation-in-part of copending U.S. application Ser. No. 923,698 filed July 11, 1978, now abandoned.

DESCRIPTION OF THE INVENTION

The present invention relates to new malonic acid esters and to a process for the preparation of malonic acid esters of the formula

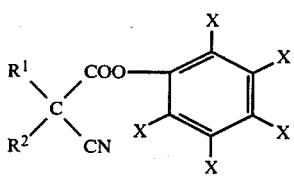

wherein $R^1$ represents hydrogen or $C_{1-6}$ alkyl, $R^2$ represents hydrogen, phenyl, thienyl, furyl, pyridyl $C_{1-6}$ alkyl, furyl-alkyl where the alkyl is $C_1$ to $C_6$ or phenylalkyl where the alkyl is $C_1$ to $C_6$ or $R^1$ and $R^2$ together form $C_1$ to $C_4$ alkylidene, furylalkylidene or phenyl-$C_1$ to $C_4$ alkylidene.

X is halogen, or a pharmaceutically acceptable salt thereof by reacting a malonic acid derivative of the formula

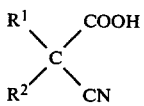

or its carboxylic acid halide with a pentahalogenophenol derivative of the formula

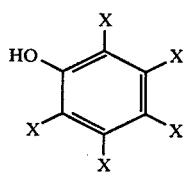

or a salt thereof.

The malonic acid derivatives of the formula I are new. The definitions of the substituents will not change in the further parts of the specification thus they will not be repeated.

In Belgian Patent Specification No. 843 106 the preparation of malonic acid and pentahalogen-phenyl esters of mono-substituted malonic acids is disclosed, but pentahalogen-phenyl esters of carboxylic acids containing a cyano group on the carbon atom next to the carboxyl group have not been prepared yet.

The term "alkyl group" as used herein means $C_{1-6}$ straight or branched saturated aliphatic hydrocarbons, such as methyl, ethyl, n-propyl, isopropyl, n-butyl, isobutyl, etc.

The term "aromatic group" stands for mono or bicyclic aromatic ring systems (such as phenyl or naphthyl group).

The term "heteroaromatic radical" stands for aromatic ring systems consisting of one or several rings, containing one or several heteroatoms (nitrogen, oxygen and/or sulphur), such as thienyl, furyl, pyridyl, pyrimidinyl, quinolyl, isoquinolyl groups etc. The aromatic and heteroaromatic rings may optionally be substituted with one or several substituents, such as halogen, such as chlorine, bromine, or iodine, or lower alkyl (such as methyl, ethyl), lower alkoxy (such as methoxy, ethoxy), halogenoalkyl (such as trifluoromethyl, amino, substituted amino (such as methylamino, ethylamino), or nitro. The term "furylalkyl group" stands for furyl-methyl, furyl-ethyl, and the term "phenyl-alkyl" may stand for benzyl, beta-phenyl-ethyl etc.

$R^1$ and $R^2$ together form an alkylene group, such as $C_{1-4}$ alkylidene, preferably methylene, or ethylidene, optionally substituted by phenyl, furyl, thienyl, pyridyl, etc. X may stand for chlorine, fluorine, or iodine, preferably for chlorine or fluorine.

The ester group in the place of $R^3$ may be any of the easily removable esterifying groups known in the chemistry of penicillins and cephalosporins, such as tri-lower alkyl-silyl or trichloroethyl. As salts of the compounds of the formula I alkali metal salts (such as sodium or potassium salts), or salts formed with organic amines (such as tri-lower alkyl amines e.g. triethylamine) may be mentioned.

Particularly interesting compounds of the formula I are those, wherein $R^1$ is a hydrogen and $R^2$ represents hydrogen or phenyl. Also interesting are compounds of the formula I, wherein $R^1$ and $R^2$ together form alkylene, preferably methylene, phenylmethylene, or furylmethylene.

As acid halides of the starting materials of the compounds of the formula II acid chlorides or bromides are preferred.

Particularly preferable compounds of the formula I are the following compounds:
cyanoacetic acid pentachlorophenyl ester,
cyanoacetic acid pentafluorophenyl ester,
α-cyano-phenylacetic acid pentachlorophenyl ester,
α-cyano-phenylacetic acid pentafluorophenyl ester,
α-cyano-β-phenyl-acrylic acid pentachlorophenyl ester,
α-cyano-β-phenyl-acrylic acid pentafluorophenyl ester.

Compounds of the formula I crystallize well and may be isolated in a pure state with a good yield without any complications. Their advantage is the good storability without decomposition and they can be used at any time for the acylation of primary amines in an apolar, aprotic medium in the presence of a tertiary base under mild reaction conditions.

According to an advantageous embodiment of the present invention salts of pentahalogenophenol with tertiary bases are used.

According to the process of the present invention the salt of pentahalogenophenol formed with a tertiary base can be reacted with a halide, preferably chloride of the malonic acid derivatives of the formula II in the presence of a halogenated solvent, preferably carbontetrachloride.

Many losses arise if the acid halides of the starting materials of the formula II are purified by distillation, as the compounds easily polymerize. The use of the crude product in the acylation reaction caused many undesired side-reactions and the preparation of the end products in the pure state was accompanied by further losses—particularly in the case of molecules sensitive to nucleophilic agents.

According to this invention halides of the acids of the formula II may be reacted without purification in a crude state.

The starting acid halides may be formed with thionyl chloride, Vilsmayer reactant, phosphoroxychloride, phosphorus pentabromide, phosphortrihalide and the obtained crude acid halide is distilled in order to remove solvents, and reacted with pentahalogenophenol and salts thereof.

The acid halides are generally prepared at a lower temperature below 50° C. in order to avoid polymerization.

When using phosphorus pentachloride in the presence of a solvent in order to prepare an acid halide, the solvent is distilled off after the reaction is completed, but it is not necessary to remove the formed phosphoroxychloride, as the ester forming process is further not disturbed by the residual phosphoroxychloride. It promotes a simple realization of the whole operation.

The acid halide is prepared by thionyl chloride in the presence of a solvent, or in the absence of a solvent, the excess thionyl chloride and the solvents are preferably distilled off at the end of the reaction before the esterification is carried out. The crude acid chloride need not be purified in this case either.

The esterification may be performed in the presence of a solvent, preferably in a halogenated solvent. Dichloromethane, alchol-free chloroform, carbontetrachloride, trichloroethylether may be used. Other ethers such as dioxan and diisopropyl ether may also be employed.

As acid binding agents a weak tertiary base is preferred, such as pyridine, N,N'-dimethyl-aniline or N-methyl-morpholine, etc.

The corresponding pentahalogenophenyl-esters are obtained with a good yield if the reaction is performed in the presence of carbontetrachloride. The stability of the pentahalogeno-phenylesters is the greatest in this solvent.

According to an advantageous embodiment of the invention pentahalogeno-phenol is dissolved in the solvent in the form of its salt formed with a tertiary base at 30°-35° C. The acid halide is added to the reaction mixture at this temperature. The formed tertiary base halide may be removed from the product by treatment with mineral acidic water, or alcohol.

The crude cyanoacetic acid pentahalogeno-phenylesters may be purified, if desired, by recrystallization.

According to another embodiment of the invention the compound of the formula II is reacted with phosphoroxychloride and pentahalogeno-phenol in a melt. The mixture is heated to 90°-110° C. until hydrochloric acid evolution ceases. The reaction mixture may be further processed as follows:

Solvent is added to the cooled melt. Halogenated solvents, e.g. dichloromethane, carbontetrachloride may be employed. After washing phosphoroxychloride, the solvent is distilled off and the residual pentahalogenophenyl ester may be isolated in a pure state after trituration with ether.

According to another embodiment of this invention compounds of the formula I may be prepared from acids of the formula II and pentahalogeno-phenol by treating the reactants together with a water abstracting agent, preferably with dicyclohexylcarbodiimide.

The reaction is preferably performed in carbontetrachloride or dichloromethane, in which the formed pentahalogeno-phenyl esters are dissolved, whereas dicyclohexyl-urea formed as a by-product may be removed by filtration.

The solvents are distilled off and the product is treated with isopropyl ether or petrolether and pure product is obtained.

The new compounds are valuable intermediates in the production of known penicillin and cephalosporin compounds with antibiotic utility.

Penam-3-carboxylic acid, 3-methyl-ceph-3-em-4-carboxylic acid and 3-acetoxy-methyl-ceph-3-em-4-carboxylic acid derivatives acylated with cyano acetic acid derivatives are known to be valuable antibiotics, which may be employed in human therapy. Particularly valuable is 7-beta-(alpha-cyano)-acetylamino-3-acetoxy-methyl-3-cephem-carboxylic acid or its sodium salt, according to formula IV hereinafter. Methods for the preparation of the above mentioned derivatives have been described according to which the amine to be acylated is acylated with acid halides or mixed anhydrides of carboxylic acids substituted with a cyano group in the alpha position. According to another known process the carboxylic acid substituted with cyano in the alpha position is reacted with the amine in the presence of a water abstracting agent, such as dicyclohexylcarbodiimide. (Swiss Patent Specification Nos.: 480,365, 542,236, 507,292.) The disadvantage of the know process is, that the preparation of pure product is generally only possible by chromatographic methods, accompanied by other technological disadvantages and problems. One of such problems occurs when using an acid chloride, as the pure acid chloride may only be prepared by a distillation accompanied by losses and the acid chloride has to be worked up immediately because of the damage of polymerization. When using a crude acid chloride to acylate molecules containing other radicals sensitive to nucleophilic agents—as it is the case with cephem and penam derivatives—many side reactions may occur.

Also many by-products are formed when employing the known mixed anhydrides, thus one should work at a rather low temperature. The pure end-product can be recovered even under such circumstances only by chromatography. Processes employing water abstracting agents are rather complicated in industry, and yields of only 65% can be achieved. It is difficult to remove the formed by-product: N-acyl ureas.

The disadvantages mentioned above are eliminated in the process of the present invention.

The present invention therefore further relates to a process for the preparation of an acid amide of the formula

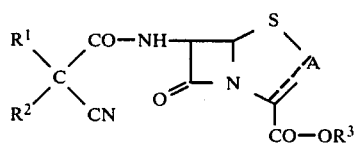

IV wherein
R¹ and R² are as defined above;
R³ is hydrogen, or a readily cleavable esterifying group, preferably trialkylsilyl, or trichloroethyl,

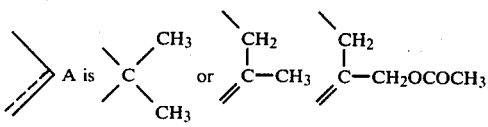

or pharmaceutically acceptable salts thereof—by acylating amines of the formula

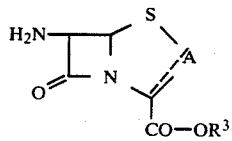

wherein $R^3$ and A are as given above—which comprises reacting amines of the formula V and salts thereof—with an ester of the formula

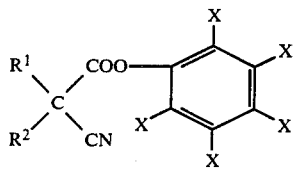

wherein $R^1$, $R^2$, $R^3$ and X as defined above, thereafter optionally splitting off the protecting group $R^3$ of the ester group in position 3 or 4 and/or setting free the product, if desired, from its salt and/or converting it to a salt thereof.

Compounds of the general formula V are preferably employed in the form of their salts, preferably in the form of sodium, potassium, lithium salts, or a salt formed with trialkylamine, such as triethylamine.

The reaction is preferably carried out in the presence of an aprotic solvent. Halogenated hydrocarbons, such as carbontetrachloride, dichloromethane, chloroform, dichloroethane may be employed. Dipolar solvents, such as acetonitrile or other solvents may also be used.

The reaction may preferably be performed in the presence of a tertiary base. Suitable bases are trialkylamines, such as triethylamine, or heterocyclic amines, such as pyridine or N-methyl-morpholine.

The active esters employed according to the present invention may be prepared by reacting the suitable cyanoacetic acid chloride with pentahalogenophenol or salts thereof. The acylation takes place generally under mild reaction conditions at a temperature of 0° to 20° C.

The product is obtained with a good yield, chromatographic purification is not necessary.

The compounds according to formula V are administered to a mammalian patient as any conventional penicillin or cephalosporin. More details may be found in U.S. Pat. No. 3,483,197.

The compounds according to formula V are administered to a patient with a bacterial infection either parenterally, intramuscularly or intravenously in a pharmaceutically effective dosage.

The appropriate compounds of the formula II may be prepared by methods known per se.

EXAMPLE 1

Cyanoacetic acid pentachlorophenyl ester 17 g. (0.2 moles) of cyanoacetic acid are mixed thorougly with 53.2 g. (0.2 moles) of pentachlorophenol, and 19.0 ml. (0.2 moles) of phosphoroxychloride are added dropwise. The obtained mixture is heated slowly on an oil-bath, until the inner temperature rises to 85° to 90° C. and the solid melts under intensive evolution of HCl. The homogeneous melt is heated until the hydrochloric acid evolution ceases. In the meantime the first cyanoacetic acid pentachlorophenyl ester precipitate is obtained. When the hydrochloric acid evolution ceases, the system is cooled and dissolved in 500 ml. of dichloromethane, washed 3 times with 100 ml. of water, treated with decolorizing charcoal, dried and evaporated. Diisopropyl ether is added. Cyanoacetic acid pentachlorophenyl ester precipitates in the form of crystals.

Yield: 47 g. (71%), m.p.: 162°–164° C.

Analysis: Calculated: C 32.42%; H 0.60%; N 4.22%; Cl 53.77%. Found: C 32.16%; H 0.61%; N 4.39%; Cl 53.40%.

EXAMPLE 2

Cyanoacetic acid pentachlorophenyl ester 8.5 g (0.1 mole) of cyano acetic acid are dissolved in 350 ml. of ethylether and cooled to 0° C. 20.1 g. (0.1 mole) of phosphorus pentachloride are added. The cooling is stopped and the temperature is slowly raised to room temperature. When the HCl evolution ceases the solvent is distilled off in vacuo. The residue containing the formed cyanoacetic acid chloride and phosphoroxychloride is taken up in 50 ml. of dichloromethane and 26 g. (0.1 mole) of pentachlorophenol and 11 ml. (0.1 mole) of N,N'-dimethylaniline are added dropwise in 300 ml. of dichloromethane.

The reaction mixture is stirred for 30 minutes and separated, the organic layer is dried, washed with 100 ml. of 2n HCl and evaporated. The residue is triturated with diisopropyl ether, filtered and air dried.

Yield: 21 g (63%), m.p.: 162°–164° C.

EXAMPLE 3

Cyanoacetic acid pentachlorophenyl ester 17 g. (0.2 moles) of cyanoacetic acid are dissolved in 150 ml. of dichloromethane and 40 g. (0.2 moles) of dicyclohexylcarbodiimide and 52 g. (0.2 moles) of pentachlorophenol dissolved in 200 ml. of dichloromethane are added dropwise at room temperature. The mixture is stirred for 4 hours at room temperature. The mixture is cooled to 0° C. and the precipitated dicyclohexylcarbodiimide is filtered and the solvent is distilled off. The residue is taken up in diisopropyl ether, filtered and dried.

Yield: 33 g (50%), m.p.: 160°–163° C.

EXAMPLE 4

Cyanoacetic acid-pentafluorophenyl ester 8.5 g. (0.1 mole) of cyanoacetic acid are dissolved in 350 ml. of ethyl ether and the solution is cooled to 0° C. 20.1 g. (0.1 mole) of phosphorus pentachloride are added. The acid chloride is formed under intensive hydrochloric acid evolution, whereafter the mixture is stirred at room temperature for two hours. When the HCl evolution ceases, the solvent is removed in vacuo.

The residue containing the formed cyanoacetic acid chloride and phosphoroxychloride is taken up in a small amount of carbontetrachloride and is added to a solution of 18.6 g. (0.1 mole) of pentafluorophenol and 8 ml. (0.1 mole) of pyridine in 300 ml. of carbontetrachloride at 25° to 30° C.

Cyanoacetic acid pentafluorophenyl ester and the formed pyridine-chlorohydrate are precipitated. The precipitates are filtered, taken up in dichloromethane and the pyridine chlorohydrate is removed by washing with 2n HCl. The dichlororomethane is removed by distillation and the precipitated crystals are triturated with petrolether, filtered, washed and dried.

Yield: 13.4 g. (53.5%), m.p.: 80°–82° C.

EXAMPLE 5

Cyanoacetic acid pentafluorophenyl ester 4.25 g. (0.05 moles) of cyanoacetic acid are dissolved in 100 ml. of dichloromethane and a solution of 10.3 g. (0.05 moles) of dicyclohexylcarbodiimide and 9.2 g. (0.05 moles) of pentafluorophenol in 50 ml. of dichloromethane is added. The mixture is stirred at room temperature for 4 hours, cooled to 0° C. and the precipitated dicyclohecylcarbodiimide is removed by filtration, the solvent is removed by distillation and the residue is taken up in petrolether and the precipitated ester is filtered, trituated with petrolether, washed and dried.

Yield: 6.3 g. (51%); m.p.: 80°–82° C.

Analysis: Calculated: C 43.0%; H 0.8%; N 5.6%; F 37.8%. Found: C 43.21%; H 1.0%; N 5.77%; F 38.0%.

EXAMPLE 6

α-Cyano-phenylacetic acid pentachlorophenylester 8 g. (0.05 moles) of α-cyano-phenylacetic acid are dissolved in 80 ml. of dichloromethane, 10.2 g. (0.05 moles) of phosphorous pentachloride are added and the mixture is stirred for 2 hours at the boiling point of the dichloromethane. The reaction is completed when the hydrochloric acid evolution ceases. The solvent is distilled off and the residue containing the obtained acid chloride and phosphoroxychloride is taken up in carbontetrachloride and the solution is added dropwise to 13 g. (0.05 moles) of pentachlorophenol and 4 ml. (0.05 moles) of pyridine dissolved in 200 ml. of carbontetrachloride. The reaction mixture is cooled and the precipitated pyridine chlorohydrate is removed by washing twice with 50 ml. of water, dried, distilled off and the residue is distilled off with diisopropyl ether. The precipitated crystalline product is cooled and filtered. The α-cyanophenylacetic acid pentachlorophenyl ester is air-dried.

Yield: 13.5 g. (68%), m.p.: 142°–144° C.

Analysis: Calculated: C 43.99%; H 1.48%; N 3.42%; Cl 43.29%. Found: C 44.10%; H 1.53%; N 3.47%; Cl 43.53%.

EXAMPLE 7

α-Cyano-phenylacetic acid-pentachlorophenyl ester 8 g. (0.05 moles) of α-cyano-phenylacetic acid are dissolved in 80 ml. of dichloromethane. 10.3 g. (0.05 moles) of dicyclohexylcarbodiimide and 13 g. (0.05 moles) of pentachlorophenol are added dropwise dissolved in 50 ml. of dichloromethane. The mixture is stirred for 4 hours, cooled to 0° C. and the precipitated dicyclohexylurea is filtered. The filtered substance is washed twice on the filter with 15 ml. of dichloromethane. The combined organic layers are distilled off and the precipitated ester is taken up with 20 ml. of diisopropyl ether and the crystals are filtered, washed twice with diisopropyl ether and dried.

Yield: 10.52 g. (53%); m.p.: 142°–144° C.

EXAMPLE 8

α-Cyano-phenylacetic acid pentachlorophenyl ester 8 g. (0.05 moles) of α-cyanophenylacetic acid, 13 g. (0.05 moles) of pentachlorophenol are mixed together. 4.3 g. (0.05 moles) of phosphoroxychloride are added dropwise. The obtained mixture is heated slowly to 85°–90° C. on an oil-bath and the mixture is kept at this temperature until the HCl evolution ceases. When the reaction is completed, the mixture is cooled to room temperature, and the melt is taken up in 100 ml. of carbon tetrachloride. The solution is washed three times with 30 ml. of water, treated with decolorizing charcoal, dried and evaporated. The product is recrystalized from diisopropyl ether, and crystalline pentachlorophenyl ester is precipitated.

Yield: 14.5 g. (73%); m.p.: 142°–144° C.

EXAMPLE 9

α-Cyano-phenylacetic acid-pentafluorophenyl ester 8 g. (0.05 moles) of α-cyano-phenylacetic acid are dissolved in 80 ml. of dichloromethane. 10.2 g. (0.05 moles) of phosphorus pentachloride are added and the mixture is stirred for two hours at the boiling point of dichloromethane. The solvent is distilled off and the residue is taken up in carbontetrachloride and the solution is added dropwise to 9.2 g. (0.05 moles) of pentafluorophenol and 4 ml. (0.05 moles) of pyridine-dissolved in 200 ml. of carbontetrachloride. The reaction mixture is cooled to 0° C. and the pyridine chlorohydrate is washed with 2n hydrochloride acid. The organic layer is washed twice with 40 ml. of water, dried over magnesium sulfate and evaporated. The α-cyanophenylacetic acid-pentafluorophenyl ester is recrystallized from petrolether Yield: 10.9 g. (67%).

Analysis: Calculated: C 55.05%; H 1.84%; N 4.28%; F 29.03%. Found: C 55.15%; H 1.97%; N 4.18%; F 28.88%.

EXAMPLE 10

α-Cyano-phenylacetic acid pentafluorophenyl ester 8 g. (0.05 moles) of α-cyano-phenylacetic acid are dissolved in dichloromethane. Under mild heating 10.3 g. (0.05 moles) of dicyclohexylcarbodiimide and 0.2 g. (0.05 moles) of pentafluorophenol dissolved in 50 ml. of dichloromethane are added dropwise. The mixture is stirred for 4 hours at 30° to 35° C. It is cooled, and the precipitated dicyclohexylurea is filtered. The substance on the filter is washed twice with 10 ml. of dichloromethane. The combined organic layers are evaporated while petrolether is added. The crystalline ester is precipitated from petrolether.

Yield: 8.46 g. (52%).

EXAMPLE 11

α-Cyano-β-phenyl-acrylic acid pentachlorophenyl ester ($R^1$ and $R^2$ together=phenyl methylene)

9.0 g. (0.05 moles) of α-cyano-β-phenyl acrylic acid are suspended in dichloromethane. 10.2 g. (0.05 moles) of phosphorous pentachloride are added and the mixture is stirred at the boiling point of the dichloromethane. The solvent is distilled off and the residue is taken up in 20 ml. of carbontetrachloride. This solution is added dropwise to a solution of 13 g. (0.05 moles) of pentachlorophenol and 4 ml. (0.05 moles) of pyridine in 200 ml. of carbontetrachloride. The reaction mixture is cooled and the pyridine chlorohydrate is washed with 50 ml. of 2n hydrochloric acid. The organic layer is washed twice with 40 ml. of water to neutral, dried over magnesium sulfate, evaporated and the residual solvent is distilled off with diisopropyl ether. The precipitated product is filtered and airdried.

Yield: 14.46 g. (68%); m.p. 152°–154° C.

Analysis: Calculated: C 45.6%; H 1.42%; N 3.32%; Cl 42.1%. Found: C 45.73%; H 1.73%; N 3.44%; Cl 41.96%.

EXAMPLE 12

α-Cyano-β-phenyl-acrylic acid pentachlorophenyl ester 9.0 g. (0.05 moles) of α-cyano-β-phenyl acrylic acid are suspended in 200 ml. of dichloromethane and to the solution 13.3 g. (0.05 moles) of dicyclohexylcarbodiimide dissolved in 100 ml. of dichloromethane are added dropwise. The mixture is boiled for 5 hours, cooled and the precipitated dicyclohexyl-urea is filtered off. It is twice washed with 10 ml. of dichloromethane. The combined organic layers are evaporated and the precipitated crystalline substance is washed with diisopropyl ether.

Yield: 11.7 g. (55%); m.p.: 152°–154° C.

EXAMPLE 13

α-Cyano-β-phenyl-acrylic acid pentafluorophenyl ester 9.0 g. (0.05 moles) of α-cyano-β-phenyl-acrylic acid are suspended in dichloromethane. 10.2 g. (0.05 moles) of phosphorus pentachloride are added and the mixture is stirred for 4 hours at the boiling point of dichloromethane.

When the hydrochloric acid evolution ceases, the reaction is completed. The solvent is distilled off and the residue containing some phosphoroxychloride is taken up in 20 ml. of carbontetrachloride. This solution is added dropwise to a solution of 9.2 g. (0.05 moles) of pentaflurorophenol and 4 ml. of pyridine (0.05 moles) in 200 ml. of carbontetrachloride. The reaction mixture is cooled and the formed pyridine chlorohydrate is washed with 50 ml. of 2n hydrochloric acid. The organic layer is washed twice with 40 ml. of water, dried over magnesium sulfate, evaporated, and the residual solvent is distilled off with petrolether. The precipitated crystalline product is filtered and washed with petrolether.

Yield: 11.57 g. (67%); m.p.: 92°–93° C.

Analysis: Calculated: C 56.65%; H 1.78%; N 4.13%; F 28.00%. Found: C 56.90%; H 1.82%; N 4.21%; F 27.67%.

EXAMPLE 14

α-Cyano-β-phenyl-acrylic acid pentafluorophenyl ester 9.0 g. (0.05 moles) of α-cyano-β-phenyl-acrylic acid are suspended in 200 ml. of dichloromethane and 9.2 g. (0.05 moles) of pentafluorophenol and 10.02 g. (0.05 moles) of dicyclohexylcarbodiimide in 100 ml. dichloromethane are added. The mixture is heated for 5 hours under reflux, cooled, the precipitated dicyclohexyl urea is filtered off. The solution is washed with 20 ml. of 2n hydrochloric acid and three times with water, dried over magnesium sulfate, evaporated and the residual oily substance is recrystallized from petrolether.

Yield: 9.5 g. (55%); m.p.: 92°–93° C.

EXAMPLE 15

7-β(α-Cyano)-acetylamino-3-acetoxymethyl-3-cephem-carboxylic acid 2.7 g. 7-amino-3-acetoxymethyl-3-cephem-carboxylic acid (7-ACA) are suspended in 50 ml. of dichloromethane and 3.5 ml. of triethylamine are added dropwise. The obtained clear solution is cooled to 0° C. and 3.3 g. (0.01 mole) of cyanoacetic acid pentachlorophenyl ester are added. The mixture is stirred for 2 hours at 0° to 5° C., and is decomposed with a buffer of pH=7. The aqueous layer is washed with ethyl acetate, the basic solution acidified with 2n HCl to pH=2 to ethyl acetate. The ethyl acetate is dried and evaporated. The product is triturated with diisopropyl ether.

Yield: 1.9 g. (88%), m.p.: 168°–170° C.

Analysis: Calculated: C 46.02%; H 3.86%; N 12.38%. Found: C 46.08%; H 3.93%; N 12.25%.

developing solvent system: 3,$R_f$=0.637 lactam C=O group: 1792 cm$^{-1}$

EXAMPLE 16

6-β(α-Cyano)β-phenylacrylamido-penam-carboxylic acid 1.1 g. (0.005 moles) of 6-APA are dissolved in 30 ml. dichloromethane by adding 1.4 ml. (0.01 mole) of triethylamine. After the dissolution is completed, 2.1 g. (0.005 moles) of α-cyano-β-phenyl-acrylic acid-pentachlorophenyl ester are added at 0° C. and the mixture is stirred for 2 hours at 0° C. The mixture is washed with saturated sodium bicarbonate and acidified into ethyl acetate with 1:3 phosphoric acid. The ethyl acetate is dried, evaporated and the precipitated product is trituated with diisopropyl ether.

Yield: 1.35 g. (72.5%); m.p.: 147°–150° C.

Analysis: Calculated: C 58.20%; H 4.61%; N 11.32%. Found: C 58.17%; H 5.03%; N 11.14%.

Developing solvent system: 2,$R_f$=0.685 lactam C=O group: 1795 cm$^{-1}$.

EXAMPLE 17

7-β-(α-Cyano)-phenylacetamido-3-methyl-3-cephem-carboxylic acid 2.2 g. (0.01 mole) of 7-ADCA are taken up in 40 ml. of acetonitrile by adding 2 drops of water and 4.2 ml. (0.03 mole)triethylamine. 3.3 g. (0.01 mole) α-cyano-phenylacetic acid-pentafluorophenyl ester are added at 0° C. The mixture is stirred for 1 hour, evaporated and taken up in ethyl acetate. The mixture is washed with saturated sodium bicarbonate, and acidified with 1:3 phosphoric acid into ethyl acetate. The solid is dried, evaporated and the precipitated crystals are precipitated with ethyl ether.

Yield: 3.2 g. (92%); m.p.: 178°–180° C.

Analysis: Calculated: C 57.14%; H 4.23%; N 11.76%. Found: C 57.20%; H 4.45%; N 11.92%.

developing solvent system: 2,$R_f$=0.678 lactam C=O group - 1790 cm$^{-1}$.

We claim:

1. A compound of the formula:

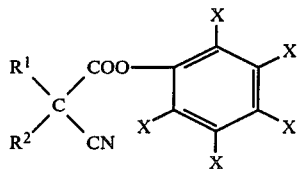

wherein
- $R^1$ is hydrogen or $C_1$ to $C_6$ alkyl;
- $R^2$ is hydrogen, phenyl, thienyl, furyl, pyridyl, $C_1$ to $C_6$ alkyl, furylalkyl where the alkyl is $C_1$ to $C_6$, or phenylalkyl where the alkyl is $C_1$ to $C_6$; or
- $R^1$ and $R^2$ together form $C_1$ to $C_4$ alkylidene, furyl-$C_1$ to $C_4$ alkylidene or phenyl-$C_1$ to $C_4$ alkylidene; and
- X is halo.

2. The compound defined in claim 1 selected from the group consisting of:
cyanoacetic acid pentachlorophenylester;
cyanoacetic acid pentafluorophenyl ester;
alpha-cyano-phenylacetic acid pentachlorophenyl ester;
alpha-cyano-phenylacetic acid pentafluorophenyl ester;
alpha-cyano-beta-phenyl-acrylic-acid pentachlorophenyl ester;
and
alpha-cyano-beta-phenyl-acrylic acid pentafluorophenyl ester.

3. The compound defined in claim 2 which is cyanoacetic acid pentachlorophenyl ester.

4. The compound defined in claim 2 which is cyanoacetic acid pentafluorophenyl ester.

5. The compound defined in claim 2 which is alpha-cyano-phenyl-acetic acid pentachlorophenyl ester.

6. The compound defined in claim 2 which is alpha-cyano-phenyl-acetic acid pentafluorophenyl ester.

7. The compound defined in claim 2 which is alpha-cyano-beta-phenyl-acrylic acid pentachlorophenyl ester.

8. The compound defined in claim 2 which is alpha-cyano-beta-phenyl-acrylic acid pentafluorophenyl ester.

9. The compound defined in claim 1 wherein $R^1$ and $R^2$ together form a methylene, furylmethylene, or phenylmethylene group.

* * * * *